(12) United States Patent
Gruenanger et al.

(10) Patent No.: US 10,889,683 B2
(45) Date of Patent: Jan. 12, 2021

(54) N,N'-DIAMINOPROPYL-2-METHYLCYCLOHEXANE-1,3-DIAMINE AND N,N'-DIAMINOPROPYL-4-METHYLCYCLOHEXANE-1,3-DIAMINE AND THE USE THEREOF AS CURING AGENTS FOR EPOXY RESINS

(71) Applicant: BASF SE, Ludwigshafen am Rhein (DE)

(72) Inventors: Christian Gruenanger, Ludwigshafen (DE); Alexander Panchenko, Ludwigshafen (DE); Irene Gorman, Ludwigshafen (DE); Veit Stegmann, Ludwigshafen (DE); Johann-Peter Melder, Ludwigshafen (DE); Norbert Gutfrucht, Ludwigshafen (DE); Martin Ernst, Ludwigshafen (DE); Marc Hofmann, Oldenburg (DE)

(73) Assignee: BASF SE, Ludwigshafen am Rhein (DE)

( * ) Notice: Subject to any disclaimer, the term of this patent is extended or adjusted under 35 U.S.C. 154(b) by 71 days.

(21) Appl. No.: 16/463,186

(22) PCT Filed: Dec. 4, 2017

(86) PCT No.: PCT/EP2017/081313
§ 371 (c)(1),
(2) Date: May 22, 2019

(87) PCT Pub. No.: WO2018/104206
PCT Pub. Date: Jun. 14, 2018

(65) Prior Publication Data
US 2020/0071456 A1    Mar. 5, 2020

(30) Foreign Application Priority Data
Dec. 5, 2016 (EP) .................... 16202180

(51) Int. Cl.
| C08G 59/50 | (2006.01) |
| C07C 209/26 | (2006.01) |
| C07C 209/84 | (2006.01) |
| C07C 211/36 | (2006.01) |

(52) U.S. Cl.
CPC ........ *C08G 59/5026* (2013.01); *C07C 209/26* (2013.01); *C07C 209/84* (2013.01); *C07C 211/36* (2013.01); *C07C 2601/14* (2017.05)

(58) Field of Classification Search
CPC .................................................. C08G 59/5026
See application file for complete search history.

(56) References Cited

U.S. PATENT DOCUMENTS

| 4,321,354 A | 3/1982 | Kluger et al. |
| 2012/0226017 A1 | 9/2012 | Pfeffinger et al. |
| 2019/0218341 A1* | 7/2019 | Reissner ............ C08G 73/0213 |

FOREIGN PATENT DOCUMENTS

| EP | 0 443 344 A2 | 8/1991 |
| EP | 0 443 344 B1 | 8/1991 |
| WO | WO 2011/032877 A1 | 3/2011 |
| WO | WO 2011/107512 A1 | 9/2011 |

OTHER PUBLICATIONS

International Search Report dated Mar. 15, 2018, in PCT/EP2017/081313 filed on Dec. 4, 2017.
Extended European Search Report dated May 19, 2017 in European Patent Application No. 16202180.2 (with English translation of Category of Cited Documents), 4 pages.
Pham, H.Q., et al., "Epoxy Resins", Ullmann's Encyclopedia of Industrial Chemistry, vol. 13, 2012, pp. 155-244.

* cited by examiner

*Primary Examiner* — Megan McCulley
(74) *Attorney, Agent, or Firm* — Oblon, McClelland, Maier & Neustadt, L.L.P.

(57) ABSTRACT

The present invention relates to the polyamines N,N'-diaminopropyl-2-methyl-cyclohexane-1,3-diamine and N,N'-diaminopropyl-4-methyl-cyclohexane-1,3-diamine and mixtures thereof, to the use thereof as curing agents for epoxy resin and to a curable composition comprising epoxy resin and these polyamines. Even at low temperatures this curing agent/the corresponding curable composition cures rapidly and is early-stage water resistant and is thus especially suitable for floor coatings. The invention further relates to the curing of this composition and the cured epoxy resin obtained by curing of this composition.

15 Claims, 1 Drawing Sheet

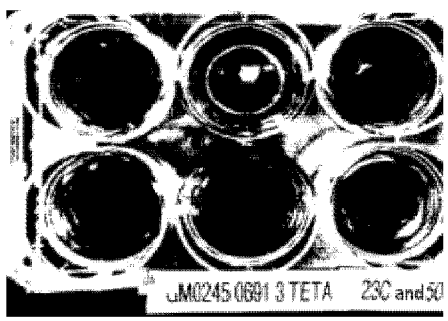
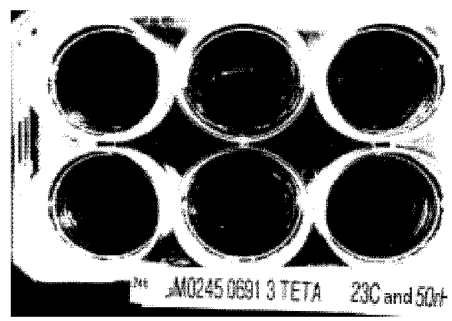
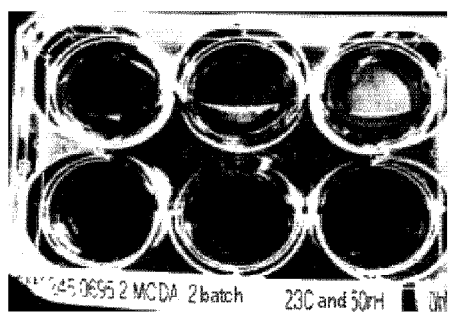
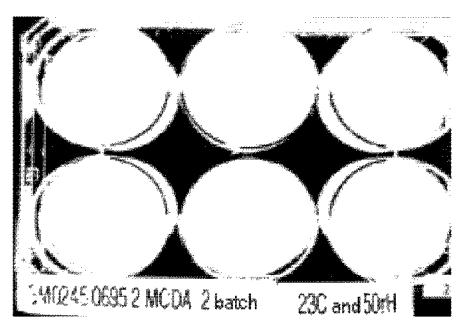
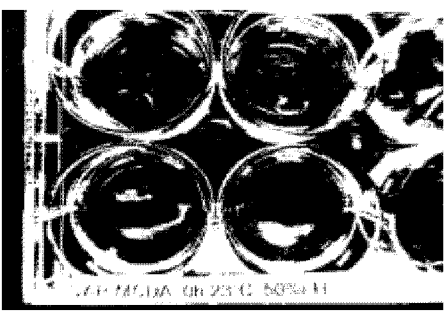
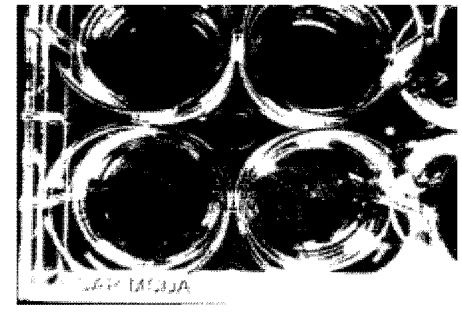

N,N'-DIAMINOPROPYL-2-METHYLCYCLOHEXANE-1,3-DIAMINE AND N,N'-DIAMINOPROPYL-4-METHYLCYCLOHEXANE-1,3-DIAMINE AND THE USE THEREOF AS CURING AGENTS FOR EPOXY RESINS

The present invention relates to the polyamines N,N'-diaminopropyl-2-methyl-cyclohexane-1,3-diamine and N,N'-diaminopropyl-4-methyl-cyclohexane-1,3-diamine and mixtures thereof, to the use thereof as curing agents for epoxy resin and to a curable composition comprising epoxy resin and these polyamines. The invention further relates to the curing of this composition and the cured epoxy resin obtained by curing of this composition.

Epoxy resins are common knowledge and on account of their toughness, flexibility, adhesion and chemicals resistance are used as materials for surface coating, as adhesives and for molding and laminating as well as for producing fiber-reinforced composite materials.

An important application of epoxy resins is surface coating and in particular floor coating (flooring). This application requires curing agents which allow rapid curing even at low temperatures. The coating shall be loadable as soon as possible after application to the surface (walkability of floor coatings), i.e. have a sufficient hardness (for example Shore D hardness). A high glass transition temperature of the coating so that the coating remains stable at high usage temperatures is also an important criterion. For a coating of surfaces exposed to moisture (for example outdoor floor coatings) good early-stage water resistance is important too.

Typical curing agents for epoxy resins are polyamines which bring about a polyaddition reaction (chain extension). Polyamines having a high reactivity are generally added only shortly before the desired curing. Such systems are therefore so-called two-component (2K) systems.

In the case of floor coatings aliphatic and cycloaliphatic polyamines in particular are used as curing agents for epoxy resins (Ullmann's Encyclopedia of Industrial Chemistry, Wiley-VCH, Weinheim, Germany, 2012, Vol. 13, Epoxy Resins, H. Pham & M. Marks (online: 15 Sep. 2005, DOI: 10.1002/14356007.a09_547.pub2)). Aliphatic polyamines such as diethylenetriamine (DETA), hexamethylenediamine (HMD) or triethylenetetramine (TETA) generally have a high reactivity and thus enable rapid curing even at room temperature or moderately elevated temperature. The cycloaliphatic polyamines such as for example isophoronediamine (IPDA), bis(4-aminocyclohexyl)methane (PACM), 1,2-diaminocyclohexane (1,2-DACH), dimethyldicyan (DMDC), 4-methylcyclohexane-1,3-diamine (4-MCDA), 2-methylcyclohexane-1,3-diamine (2-MCDA) or a mixture of 2-MCDA and 4-MCDA (MCDA) typically react somewhat more slowly which is generally also reflected in a longer pot life. Epoxy resins cured with cycloaliphatic amines typically feature relatively good electrical, mechanical and thermal properties, such as in particular a relatively high glass transition temperature (Tg).

While curing of epoxy resins with 1,2-DACH does allow for high glass transition temperatures its high volatility and toxicity (in particular skin sensitization) make the use of this amine problematic. U.S. Pat. No. 4,321,354 therefore provides as a curing agent an aminopropyl-substituted derivative of 1,2-DACH which is said to be less volatile and toxic.

MCDA, the use of which for curing epoxy resins has likewise been described (EP-B 443344; WO 2011/032877), is much less volatile and toxic than 1,2-DACH.

There is a need for an aminic curing agent for curing epoxy resins for floor coating applications which combines the rapid curing of aliphatic polyamines, in particular at low temperatures such as room temperature or below or at moderately elevated temperatures such as 75° C., with the good thermal properties (high glass transition temperature) of cycloaliphatic polyamines. Such a curing agent should be employable in particular also in the low temperature range and there allow rapid curing where a relatively high hardness (for example Shore D hardness) is achieved as rapidly as possible. There is also a need for such a curing agent to exhibit good early-stage water resistance.

The present invention may accordingly be considered to have for its object to provide such an aminic curing agent suitable for curing epoxy resins especially for floor coating applications which combines rapid curing even at low temperatures, good thermal and mechanical properties and good early-stage water resistance.

The present invention accordingly relates to the provision of a polyamine selected from the group consisting of N,N'-diaminopropyl-2-methyl-cyclohexane-1,3-diamine (DAP-2-MCDA) and N,N'-diaminopropyl-4-methyl-cyclohexane-1,3-diamine (DAP-4-MCDA). In a particular embodiment the present invention relates to mixtures of these polyamines (DAP-MCDA).

The molecular structure of DAP-2-MCDA and DAP-4-MCDA is recited in the following formulae:

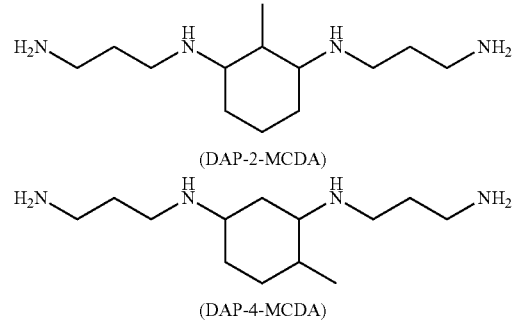

The present invention further relates to a process for producing DAP-2-MCDA, DAP-4-MCDA or DAP-MCDA, comprising step 1 in which 2-MCDA, 4-MCDA or MCDA is reacted with acrylonitrile to afford the corresponding cyanoethylated intermediate and step 2 in which the cyanoethylated intermediate is subjected to catalytic hydrogenation with hydrogen to afford DAP-2-MCDA, DAP-4-MCDA or DAP-MCDA.

The 2-MCDA, 4-MCDA or MCDA employed in step 1 of the production process according to the invention is obtainable by ring hydrogenation of 2,6-toluenediamine (2,6-TDA), 2,4-toluenediamine (2,4-TDA) or a mixture of 2,4- and 2,6-TDA (EP-B 443344; WO 2011/032877).

The reaction in step 1 of the production process according to the invention is preferably carried out at a temperature of 20° C. to 100° C. In one variant of the production process according to the invention the acrylonitrile is employed in a superstoichiometric amount in step 1 and the excess acrylonitrile after reaction with the 2-MCDA, 4-MCDA or MCDA is reacted with a low molecular weight amine such as for example dimethylamine. It is preferable when a Raney catalyst, for example a cobalt Raney catalyst, is used for the hydrogenation in step 2 of the production process according to the invention. The hydrogenation in step 2 of the production process according to the invention is preferably carried out at a hydrogen partial pressure of 20 to 200 bar absolute. The hydrogenation in step 2 of the production process according to the invention is preferably carried out at a temperature of 80° C. to 150° C. In one variant of the production process according to the invention the cyanoethylated intermediate obtained in step 1 is purified, for example by distillation, in a step 1a prior to further use in step 2. The DAP-2-MCDA, DAP-4-MCDA or DAP-MCDA obtained in step 2 of the production process according to the invention is preferably purified, for example by distillation, in a subsequent step 2a.

The present invention further relates to a curable composition comprising one or more epoxy resins and one or more polyamines selected from the group consisting of DAP-2-MCDA and DAP-4-MCDA.

Epoxy resins according to the present invention typically have 2 to 10, preferably 2 to 6, very particularly preferably 2 to 4, and in particular 2, epoxy groups. The epoxy groups are in particular glycidyl ether groups such as are formed in the reaction of alcohol groups with epichlorohydrin. The epoxy resins may be low molecular weight compounds generally having an average molar weight ($M_n$) of less than 1000 g/mol, or higher molecular weight compounds (polymers). Such polymeric epoxy resins preferably have a degree of oligomerization of 2 to 25, particularly preferably of 2 to 10, units. Said resins may be aliphatic or cycloaliphatic compounds or compounds comprising aromatic groups. In particular, the epoxy resins are compounds comprising two aromatic or aliphatic 6-membered rings or oligomers thereof. Epoxy resins obtainable by reaction of epichlorohydrin with compounds having at least two reactive H atoms, in particular with polyols, are of industrial importance. Epoxy resins obtainable by reaction of epichlorohydrin with compounds comprising at least two, preferably two, hydroxy groups and two aromatic or aliphatic 6-membered rings are of particular importance. Such compounds include in particular bisphenol A and bisphenol F and also hydrogenated bisphenol A and bisphenol F—the corresponding epoxy resins are the diglycidyl ethers of bisphenol A or bisphenol F, or hydrogenated bisphenol A or bisphenol F. Preferably employed as the epoxy resin according to the present invention is an epoxy resin selected from the group consisting of diglycidyl ether of bisphenol A, diglycidyl ether of bisphenol F, diglycidyl ether of hydrogenated bisphenol A and diglycidyl ether of hydrogenated bisphenol F. Typically employed as the epoxy resin according to the present invention is bisphenol A diglycidylether (DGEBA). Suitable epoxy resins according to the present invention also include tetraglycidyl methylenedianiline (TGMDA) and triglycidyl aminophenol or mixtures thereof. Also contemplated are reaction products of epichlorohydrin with other phenols, for example with cresols or phenol-aldehyde adducts, such as phenol-formaldehyde resins, in particular novolacs. Epoxy resins not derived from epichlorohydrin are also suitable. Examples of contemplated resins include epoxy resins comprising epoxy groups due to reaction with glycidyl (meth)acrylate. It is preferable according to the invention to employ epoxy resins or mixtures thereof that are liquid at room temperature (25° C.). The epoxy equivalent weight (EEW) indicates the average mass of the epoxy resin in g per mole of epoxy group.

It is preferable when the curable composition according to the invention consists to an extent of at least 50% by weight of epoxy resin.

The curable composition according to the invention may comprise one or more reactive diluents. Reactive diluents in the context of the invention are compounds which reduce the initial viscosity of the curable composition and which, in the course of the curing of the curable composition, form a chemical bond with the incipient network of epoxy resin and curing agent. Preferred reactive diluents in the context of the present invention are low molecular weight organic, preferably aliphatic, compounds having one or more epoxy groups and also cyclic carbonates, in particular cyclic carbonates having 3 to 10 carbon atoms, for example ethylene carbonate, propylene carbonate, butylene carbonate or vinylene carbonate. Reactive diluents according to the invention are preferably selected from the group consisting of ethylene carbonate, vinylene carbonate, propylene carbonate, 1,4-butanediol bisglycidyl ether, 1,6-hexanediol bisglycidyl ether (HDDE), glycidyl neodecanoate, glycidyl versatate, 2-ethylhexyl glycidyl ether, neopentyl glycol diglycidyl ether, p-tert-butyl glycidyl ether, butyl glycidyl ether, $C_8$-$C_{10}$-alkyl glycidyl ether, $C_{12}$-$C_{14}$-alkyl glycidyl ether, nonylphenyl glycidyl ether, p-tert-butylphenyl glycidyl ether, phenyl glycidyl ether, o-cresyl glycidyl ether, polyoxypropylene glycol diglycidyl ether, trimethylolpropane triglycidyl ether (TMP), glycerol triglycidyl ether, triglycidylparaaminophenol (TGPAP), divinylbenzyl dioxide and dicyclopentadiene diepoxide. Said diluents are preferably selected from the group consisting of 1,4-butanediol bisglycidyl ether, $C_8$-$C_{10}$-alkyl monoglycidyl ether, $C_{12}$-$C_{14}$-alkyl monoglycidyl ether, 1,6-hexanediol bisglycidyl ether (H DDE), neopentyl glycol diglycidyl ether, trimethylolpropane triglycidyl ether (TMP), glycerol triglycidyl ether and dicyclopentadiene diepoxide.

The reactive diluents according to the invention preferably account for a proportion of up to 30% by weight, particularly preferably up to 25% by weight, in particular up to 20% by weight, based on the resin component (epoxy resin and any employed reactive diluents) of the curable composition. In a particular embodiment the reactive diluents according to the invention account for at least 5% by weight, in particular at least 10% by weight, based on the resin component (epoxy resin and any employed reactive diluents) of the curable composition.

In addition to DAP-2-MCDA, DAP-4-MCDA or DAP-MCDA the curable composition according to the invention may also comprise one or more further aminic curing agents. DAP-2-MCDA, DAP-4-MCDA or DAP-MCDA preferably accounts for at least 50% by weight, particularly preferably at least 80% by weight, very particularly preferably at least 90% by weight, based on the total amount of the aminic curing agents (DAP-2-MCDA, DAP-4-MCDA or DAP-MCDA and any further aminic curing agents) in the curable composition. In a particular embodiment the curable composition comprises no further aminic curing agents in addition to DAP-2-MCDA, DAP-4-MCDA or DAP-MCDA. In the context of the present invention an aminic curing agent is to be understood as meaning an amine having an NH-functionality of 2 (thus for example a primary monoamine has an NH-functionality of 2, a primary diamine has an NH-functionality of 4 and an amine having 3 secondary amino groups has an NH functionality of 3).

In the curable composition according to the invention it is preferable when the epoxy resins (including any reactive diluents with their respective reactive groups) and aminic curing agents are employed in an approximately stoichiometric ratio based on the reactive groups of the compounds of the resin component (epoxy groups and for example any carbonate groups) and the NH-functionality. Particularly suitable ratios of reactive groups of the compounds of the resin component to NH-functionality are for example 1:0.8 to 1:1.2. Reactive groups of the compounds of the resin component are groups which undergo chemical reaction with the amino groups of the aminic curing agent under the curing conditions.

The curable composition according to the invention may also comprise one or more further additions such as for example inert diluents, curing accelerators, reinforcing fibers (in particular glass or carbon fibers), pigments, colorants, fillers, release agents, tougheners, flow agents, antifoams, flame retardants or thickeners. Such additions are typically added in functional amounts, i.e., for example, a pigment is typically added in an amount which results in the composition attaining the desired color. The compositions according to the invention generally comprise from 0% to 50% by weight, preferably 0% to 20% by weight, for example 2% to 20% by weight for the entirety of all additives based on the total curable composition. In the context of the present invention additives are to be understood as meaning any additions to the curable composition which are neither epoxy compound nor reactive diluent nor aminic curing agent.

The invention further provides a process for producing cured epoxy resins from the curable composition according to the invention. In this process the curable composition according to the invention is provided and subsequently cured. To this end the components (epoxy resin and curing agent (comprising DAP-2-MCDA and/or DAP-4-MCDA) and optionally further components such as for example reactive diluents, reaction accelerants or other additives) are contacted with one another, mixed and subsequently cured at a temperature practicable for the application. The curing is preferably carried out at a temperature of at least 0° C., particularly preferably of at least 10° C.

The invention especially provides a process for producing coatings, in particular floor coatings, wherein the curable composition according to the invention is provided, applied to a surface and subsequently cured. To this end the components (epoxy resin, curing agent (comprising DAP-2-MCDA and/or DAP-4-MCDA) and optionally further components such as for example reactive diluents, reaction accelerants or other additives) are contacted with one another, mixed, applied to a surface and subsequently cured at a temperature practicable for the application. The curing is preferably carried out at a temperature of at least 0° C., particularly preferably of at least 10° C.

The cured epoxy resin is preferably also subjected to a thermal aftertreatment, for example in the context of the curing or in the context of an optional downstream heat treatment.

The curing may be carried out at standard pressure and at temperatures of less than 250° C., in particular at temperatures of less than 185° C., preferably at temperatures of less than 100° C., in particular in a temperature range from 0° C. to 185° C., very particularly preferably in a temperature range from 10° C. to 130° C., very particularly preferably in a temperature range from 10° C. to 75° C., in particular in a temperature range from 10° C. to 35° C.

The invention further relates to the cured epoxy resin made of the curable composition according to the invention. The process especially provides cured epoxy resin obtainable/obtained by curing of a curable composition according to the invention. The process especially provides cured epoxy resin obtainable/obtained by the process according to the invention for producing cured epoxy resins.

The curable compositions according to the invention are suitable as a coating composition or impregnating composition, as an adhesive, for producing molded articles and composite materials or as casting compositions for embedding, bonding or consolidating molded articles. Coating compositions include for example lacquers. The curable compositions according to the invention may in particular be used to obtain scratch-resistant protective lacquers on any desired substrates, for example made of metal, plastic or wood materials. The curable compositions are also suitable as insulating coatings in electronic applications, for example as insulating coating for wires and cables. Their use for producing photoresists may also be mentioned. They are also suitable as repair lacquer, for example also in the repair of pipes without deinstallation of the pipes (cure in place pipe (CIPP) rehabilitation).

The curable compositions according to the invention are suitable for curing in the presence of water or atmospheric humidity on account of their early-stage water resistance. The present invention thus also provides a process for producing cured epoxy resins from the curable composition according to the invention, wherein the curing is carried out in the presence of water or atmospheric humidity, in particular of atmospheric humidity, in particular with a relative atmospheric humidity of at least 30%, very particularly with a relative atmospheric humidity of at least 50%.

In the case of curing in the low temperature range (for example 0° C. to 30° C.) the curable compositions according to the invention combine a relatively high Shore D hardness, which is also achieved relatively rapidly, with a relatively short gel time. Said compositions simultaneously exhibit a very good early-stage water resistance. This profile of properties makes the curable compositions according to the invention especially suitable for floor coatings.

The present invention further provides for the use of one or more polyamines selected from the group consisting of DAP-2-MCDA and DAP-4-MCDA as a curing agent for epoxy resins, in particular as a curing agent for producing epoxy resin-based coatings, in particular floor coatings (flooring).

In the context of the present invention the term room temperature is to be understood as meaning a temperature of 23° C.

The glass transition temperature (Tg) may be determined by dynamic-mechanical analysis (DMA), for example according to the standard DIN EN ISO 6721, or with a differential calorimeter (differential scanning calorimetry; DSC), for example according to the standard DIN 53765. In DMA a rectangular test specimen is subjected to torsional stress with an enforced frequency and predetermined strain. The temperature is increased via a defined temperature ramp and storage and loss moduli are recorded at fixed time intervals. The former represents the stiffness of a viscoelastic material. The latter is proportional to the work dissipated in the material. The phase shift between dynamic stress and dynamic strain is characterized by the phase angle $\delta$. The glass transition temperature may be determined by various methods. As the maximum of the tan $\delta$ curve, as the maximum of the loss modulus or by the tangent method via the storage modulus. When determining glass transition temperature using a differential calorimeter a very small sample quantity (about 10 mg) is heated in an aluminum crucible and the heat flow to a reference crucible is measured. This cycle is repeated and determination of the glass transition is carried out in the second cycle. Evaluation of the Tg step of the heat flow curve may be determined via the inflection point, according to the half width or according to the middle point temperature method.

The gel time according to DIN 16 945 provides a reference point relating to the period between the addition of the curing agent to the reaction mixture and the transition of the reaction resin composition from the liquid state to the gel state. The temperature plays an important role, and the gel time is therefore determined for a predetermined temperature in each case. Dynamic-mechanical methods, in particular rotational viscometry, make it possible to analyze even small sample quantities in quasi-isothermal fashion and to capture their entire viscosity/stiffness profile. According to the standard ASTM D 4473 the point of intersection between the storage modulus G' and the loss modulus G" at which the damping tan δ has a value of 1 is the gel point and the period between addition of the curing agent to the reaction mixture and achievement of the gel point is the gel time. The thus-determined gel time may be regarded as a measure of the curing time.

Shore hardness is a characteristic of polymers such as for example cured epoxy resins which is directly related to the penetration depth of a penetrating body (indenter) into the test specimen and is thus a measure of the hardness of the test specimen. It is determined for example according to the standard DIN ISO 7619-1. A distinction is made between the methods Shore A, C and D. A spring-loaded pin made of hardened steel is used as the indenter. The indenter is pressed into the test specimen with spring force and the penetration depth represents a measure of the Shore hardness. While determination of Shore A and C hardness employs as the indenter a frustocone having an end-face of 0.79 mm in diameter and an opening angle of 35°, Shore D hardness testing employs as the indenter a frustocone having a spherical tip having a radius of 0.1 mm and an opening angle of 30°. To determine Shore hardness parameters a scale from 0 Shore (2.5 mm penetration depth) to 100 Shore (0 mm penetration depth) was introduced. A value of 0 represents the maximum possible impression, i.e. the material provides no resistance to the penetration of the indenter. By contrast, a value of 100 represents a very high resistance of the material to penetration and essentially no impression is produced.

Temperature plays a decisive role when determining Shore hardness and the measurements must therefore be performed in accordance with the standard over a limited temperature range of for example 23° C.±2° C. In the case of floor coatings it is typically considered that the floor is walkable again above a Shore D hardness of 45.

Early-stage water resistance is the property of a coating to be contactable with water or atmospheric humidity without damage to the coating after only a short time from application. In the case of coatings based on epoxy resins and aminic curing agents such damage refers in particular to carbamate formation which is apparent from the formation of white streaks or crusts on the surface of the fresh coating ("blushing" and "blooming").

FIGURES

FIG. 1 shows the result of carbamate formation according to example 5 for the curing agents TETA (upper images), MCDA (middle images) and DAP-MCDA (lower images), in each case at commencement of the test (left hand side) and after 24 hour incubation at room temperature and 50% relative atmospheric humidity (right-hand side). Clearly apparent is the white clouding which has formed after incubation in the MCDA test dishes. By contrast, the batches with TETA and DAP-MCDA remained unclouded.

EXAMPLES

Example 1

Production of DAP-MCDA 572 g (4.5 mol) of MCDA (Baxxodur EC210, BASF), an isomer mixture of 4-MCDA and 2-MCDA produced by ring hydrogenation of a mixture of 2,6-tolylene diamine (15-25%) and 2,4-tolylene diamine (75-85%) over a suspended ruthenium catalyst at 230° C. and 230 bar of hydrogen pressure were initially charged into a stirred vessel together with water (76.2 g). Acrylonitrile (474.9 g; 9.0 mol) was added at 26° C. over a period of 7 h, causing the temperature of the reaction mixture to increase slightly to 31° C. The reaction mixture was stirred at 60° C. over a period of 12 h. Since complete conversion was not yet detected additional acrylonitrile (45 g; 0.9 mol) was added at 60° C. and the mixture was stirred for a further 16 h. Excess acrylonitrile was reacted with an aqueous dimethylamine solution (40%; 95.5 g, 0.85 mol) at 60° C. The low boilers were removed from the reaction mixture by distillation at 3.5 mbar and 200° C. bottoms temperature and the thus-obtained biscyanoethylated intermediate was employed in the subsequent hydrogenation.

50 g of the biscyanoethylated intermediate were transferred into a stirred autoclave. A Raney cobalt catalyst (5 g) was employed as the hydrogenation catalyst. Tetrahydrofuran (75 g) was used as solvent and sodium hydroxide (50% in water; 0.1 g) was added as an additive. The autoclave was sealed and purged twice with nitrogen. The mixture was then heated to 120° C. and a pressure of 100 bar was applied with hydrogen. The hydrogenation was performed over a period of 5 h and the autoclave was subsequently cooled and decompressed. The catalyst was filtered off and the solvent THF was removed using a rotary evaporator. Several batches were combined and the product (DAP-MCDA) was purified by distillation. 232 g of crude material afforded 129 g of the target product in a purity of >98% (analysis by GC area %).

Example 2

Curing of Epoxy Resin with DAP-MCDA

DAP-MCDA from example 1 and epoxy resin (bisphenol A diglycidyl ether, Epilox A19-03, Leuna, EEW: 184 g/mol) were mixed in a stoichiometric ratio in a stirrer (1 min at 2000 rpm). DSC measurements (differential scanning calorimetry) and rheological analyses were performed immediately after mixing. For comparison, corresponding compositions comprising TETA (Akzo-Nobel) and MCDA (BASF) were also analyzed in the same way. The DSC analyses of the curing reaction of DAP-MCDA or TETA or MCDA for determining onset temperature (To), maximum temperature (Tmax), exothermic energy (ΔH) and glass transition temperatures (Tg) were performed according to ASTM D 3418 using the following temperature profile: 0° C.→5K/min 180° C.→30 min 180° C.→20K/min 0° C.→20K/min 220° C. The 2nd run used the following temperature profile: 0° C.→20K/min 220° C. Tg was determined in the 2nd run. The results are summarized in table 1.

The rheological measurements for investigating the reactivity profile of the different aminic curing agents (TETA, MCDA and DAP-MCDA) with the epoxy resin were performed at various temperatures using a plate-plate rheometer (MCR 301, Anton Paar) under shear stress control having a plate diameter of 15 mm and a slot width of 0.25 mm. The time (pot life, as a measure for the period in which the reaction resin composition is handleable) required by the freshly produced reaction resin composition to achieve a viscosity of 10 000 mPa*s at a defined temperature was measured. The measurement was performed in rotation at different temperatures (10° C., 23° C. and 75° C.) using the abovementioned rheometer. The initial viscosity (averaged over a period of 2 to 5 min after mixing of the components) for the respective mixtures at the respective temperatures was determined simultaneously. Finally the gel times were determined. These measurements were performed in oscillation at 10° C., 23° C. and 75° C. using the abovementioned rheometer. The point of intersection of loss modulus (G") and storage modulus (G') provides the gel time. The results of the rheological measurements are summarized in table 2.

TABLE 1

Exothermicity profile and glass transition temperature for the curing of epoxy resin with DAP-MCDA/for comparison with TETA or MCDA

|  | To (° C.) | Tmax (° C.) | ΔH (J/g) | Tg (° C.) |
| --- | --- | --- | --- | --- |
| TETA | 62 | 90 | 570 | 141 |
| MCDA | 78 | 108 | 528 | 169 |
| DAP-MCDA | 68 | 98 | 540 | 152 |

TABLE 2

Rheological profile for the curing of epoxy resin with DAP-MCDA/for comparison with TETA or MCDA

|  |  | Initial viscosity (mPa*s) | Pot life (min) | Gel time (min) |
| --- | --- | --- | --- | --- |
| 10° C. | TETA | 9931 | n.a. | 693 |
|  | MCDA | 6096 | 83 | 1830 |
|  | DAP-MCDA | 18 573 | n.a. | 910 |
| 23° C. | TETA | 2098 | 58 | 282 |
|  | MCDA | 1290 | 160 | 727 |
|  | DAP-MCDA | 3170 | 58 | 365 |
| 75° C. | TETA | 88 | 7 | 11 |
|  | MCDA | 56 | 20 | 52 |
|  | DAP-MCDA | 197 | 9 | 15 | n.a.: not applicable.

The gel time as a measure for the curing time differs markedly for the employed curing agents (DAP-MCDA and TETA or MCDA for comparison). Compared to MCDA, DAP-MCDA exhibits a markedly reduced pot life and gel time. The glass transition temperature achieved for DAP-MCDA curing is markedly higher than that achieved for TETA curing.

Example 3

Mechanical Properties of the Epoxy Resin Cured with DAP-MCDA

DAP-MCDA from example 1 and epoxy resin (bisphenol A diglycidyl ether, Epilox A19-03, Leuna, EEW: 184 g/mol) were mixed in a stoichiometric ratio in a stirrer (1 min at 2000 rpm) and subsequently cured at elevated temperature (2 h 80° C., 3 h 125° C.). The mechanical parameters (tensile modulus (E-t), tensile strength (σ-M), tensile elongation (ε-M), flexural modulus (E-f), flexural strength (α-fM), flexural elongation (ε-fM)) were determined according to ISO 527-2:1993 and ISO 178:2006. For comparison, corresponding compositions comprising TETA (TETA, Akzo-Nobel) and MCDA (Baxxodur EC210, BASF) were also analyzed in the same way.

TABLE 3

Mechanical properties of epoxy resin cured with DAP-MCDA compared to epoxy resin cured with TETA or MCDA

|  | Elongation test | | | Flexural test | | |
| --- | --- | --- | --- | --- | --- | --- |
|  | E-t (MPa) | σ-M (MPa) | ε-M (%) | E-f (MPa) | σ-fM (MPa) | ε-fM (%) |
| TETA | 2882 | 73 | 7 | 2991 | 110 | 6 |
| MCDA | 2894 | 86 | 7 | 2889 | 125 | 6 |
| DAP-MCDA | 2704 | 72 | 5 | 2790 | 105 | 6 |

The values for tensile modulus, flexural modulus, tensile strength and flexural strength are slightly lower for the epoxy resin cured with DAP-MCDA compared to the epoxy resin cured with MCDA or the epoxy resin cured with TETA.

Example 4

Shore D Hardness of the Epoxy Resin Cured with DAP-MCDA

DAP-MCDA from example 1 and epoxy resin (bisphenol A diglycidyl ether, Epilox A19-03, Leuna, EEW: 184 g/mol) were mixed in a stoichiometric ratio in a stirrer (1 min at 2000 rpm) and subsequently cured over a period of 8 days at room temperature (23° C.) and at 10° C. (climate test cabinet at 65% relative humidity). Over this time (after 1, 2, 3 and 8 days) the Shore D hardness of the test specimens (thickness 35-36 mm) was determined according to DIN ISO 7619-1 using a durometer (TI Shore test rig, Sauter Messtechnik). For comparison, corresponding compositions comprising TETA (TETA, Akzo-Nobel) and MCDA (Baxxodur EC210, BASF) were also analyzed in the same way.

TABLE 4

Shore D hardness of epoxy resin cured with DAP-MCDA compared to epoxy resin cured with TETA or MCDA

|  | 5 h | 6 h | 8 h | 9 h | 10 h | 1 day | 2 days | 3 days | 8 days |
| --- | --- | --- | --- | --- | --- | --- | --- | --- | --- |
| at room temperature | | | | | | | | | |
| TETA | 80 | 84 | 84 | 84 | 84 | 86 | 86 | 86 | 86 |
| MCDA | n.d. | n.d. | 64 | 79 | 84 | 84 | 84 | 84 | 85 |
| DAP-MCDA | n.d. | 76 | 83 | 85 | 86 | 86 | 87 | 87 | 88 |
| at 10° C. | | | | | | | | | |
| TETA |  |  |  |  |  | 75 | 83 | 84 | 85 |
| MCDA |  |  |  |  |  | n.d. | 69 | 78 | 79 |
| DAP-MCDA |  |  |  |  |  | 82 | 82 | 83 | 84 | n.d.: not determinable

DAP-MCDA-cured resin develops a high Shore D hardness at a rate that is distinctly faster than MCDA and approximately comparable to TETA-cured resin. The high Shore D hardness is also achieved very rapidly even at low temperatures such as 10° C.

Example 5

Carbamate Formation

DAP-MCDA, and for comparison TETA and MCDA, were filled into dishes and incubated at a temperature of 23° C. and a relative atmospheric humidity of 50% in a climate test cabinet. Formation of carbamate (whitish precipitate) was tested by visual inspection after 24 h. While distinct carbamate formation was observable in the case of MCDA, no signs of carbamate formation were apparent in the case of DAP-MCDA and TETA (FIG. 1). Carbamate formation is a sign of insufficient early-stage water resistance. DAP-MCDA and TETA thus exhibit very good early-stage water resistance in contrast to MCDA.

The invention claimed is:

1. A polyamine, selected from the group consisting of N,N'-diaminopropyl-2-methylcyclohexane-1,3-diamine and N,N'-diaminopropyl-4-methyl-cyclohexane-1,3-diamine.

2. A curing agent, comprising one or more polyamines of claim 1.

3. A process for producing the polyamine of claim 1 or a mixture comprising the polyamine, the process comprising:
reacting 2-methyl-cyclohexane-1,3-diamine, 4-methyl-cyclohexane-1,3-diamine or a mixture of 2-methyl-cyclohexane-1,3-diamine and 4-methyl-cyclohexane-1,3-diamine with acrylonitrile to obtain a cyanoethylated intermediate, and
subjecting the cyanoethylated intermediate to catalytic hydrogenation with hydrogen to afford obtain N,N'-diaminopropyl-2-methyl-cyclohexane-1,3-diamine, N,N'-diaminopropyl-4-methyl-cyclohexane-1,3-diamine or a mixture of N'-diaminopropyl-2-methyl-cyclohexane-1,3-diamine and N,N'-diaminopropyl-4-methyl-cyclohexane-1,3-diamine.

4. The process of claim 3, wherein the cyanoethylated intermediate is purified prior to the subjecting.

5. The process of claim 3, further comprising purifying the N,N'-diaminopropyl-2-methylcyclohexane-1,3-diamine, the N,N'-diaminopropyl-4-methyl-cyclohexane-1,3-diamine or the mixture of N'-diaminopropyl-2-methyl-cyclohexane-1,3-diamine and N,N'-diaminopropyl-4-methyl-cyclohexane-1,3-diamine.

6. The process of claim 3, wherein a Raney catalyst is used for the catalytic hydrogenation.

7. A curable composition, comprising
one or more epoxy resins and
one or more polyamines of claim 1.

8. The curable composition of claim 7, wherein the one or more epoxy resins are selected from the group consisting of diglycidyl ether of bisphenol A, diglycidyl ether of bisphenol F, diglycidyl ether of hydrogenated bisphenol A and diglycidyl ether of hydrogenated bisphenol F.

9. The curable composition of claim 7, wherein said composition comprises one or more reactive diluents.

10. The curable composition of claim 7, wherein in addition to the one or more polyamines, said composition also comprises one or more aminic curing agents.

11. The curable composition of claim 7, wherein said composition also comprises one or more further additions.

12. A process for producing a cured epoxy resin, the process comprising providing and subsequently curing a curable composition of claim 7.

13. The process of claim 12, wherein the curing is carried out in the presence of atmospheric humidity.

14. A cured epoxy resin, obtainable by the process of claim 12.

15. A cured epoxy resin, obtainable by curing the curable composition of claim 7.

* * * * *